United States Patent [19]

Eberlein et al.

[11] 4,137,318

[45] Jan. 30, 1979

[54] N-(PHENYLALKYLAMINO-ALKYL)-DIHYDROISOQUINOLINONES, PHARMACEUTICAL COMPOSITIONS AND METHODS EMPLOYING THEM

[75] Inventors: Wolfgang Eberlein, Biberach; Joachim Heider, Warthausen; Volkhard Austel, Biberach; Jürgen Dämmgen, Warthausen; Rudolf Kadatz, Biberach, all of Germany

[73] Assignee: Boehringer Ingelheim GmbH, Ingelheim am Rhein, Germany

[21] Appl. No.: 826,853

[22] Filed: Aug. 22, 1977

[30] Foreign Application Priority Data

Sep. 3, 1976 [DE] Fed. Rep. of Germany ....... 2639718

[51] Int. Cl.² ................ A61K 31/47; C07D 217/24; C07D 223/16; A61K 31/55
[52] U.S. Cl. ................ 424/258; 260/239.3 B; 424/244; 546/90; 546/141
[58] Field of Search ........ 260/288 CE, 288 D, 288 A, 260/288 CF; 424/258

[56] References Cited

U.S. PATENT DOCUMENTS

| | | | |
|---|---|---|---|
| 3,600,394 | 8/1971 | Coyne et al. | 260/288 D |
| 3,947,451 | 3/1976 | Jönsson et al. | 260/281 R |
| 3,948,898 | 4/1976 | Kutter et al. | 260/268 BQ |
| 4,021,558 | 5/1977 | Kutter et al. | 424/258 |
| 4,029,795 | 6/1977 | Eichenberger et al. | 424/258 |

*Primary Examiner*—Donald G. Daus
*Assistant Examiner*—Diana G. Rivers
*Attorney, Agent, or Firm*—Hammond & Littell

[57] ABSTRACT

Compounds of the formula

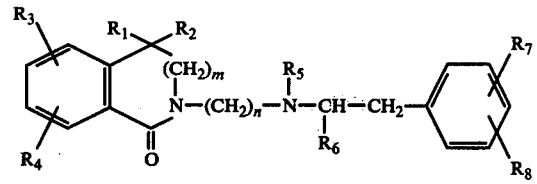

wherein
$R_1$, $R_2$ and $R_6$, which may be identical to or different from each other, are each hydrogen or lower alkyl;
$R_3$ is lower alkoxy;
$R_4$ is lower alkoxy or, together with $R_3$, methylenedioxy or ethylenedioxy;
$R_5$ is hydrogen, lower alkyl or benzyl;
$R_7$ is hydrogen or lower alkoxy;
$R_8$ is hydrogen, lower alkoxy or, together with $R_7$, methylenedioxy or ethylenedioxy;
m is 1 or 2; and
n is 2 or 3;
and non-toxic, pharmacologically acceptable acid addition salts thereof. The compounds as well as their salts are useful as antihypertensives and heart rate reducers.

6 Claims, No Drawings

N-(PHENYLALKYLAMINO-ALKYL)-DIHYDROISOQUINOLINONES, PHARMACEUTICAL COMPOSITIONS AND METHODS EMPLOYING THEM

This invention relates to novel N-(phenylalkylaminoalkyl)-dihydroisoquinolinones and -tetrahydrobenzazepinones and acid addition salts thereof, as well as to various methods of preparing these compounds.

More particularly, this invention relates to a novel class of N-substituted dihydroisoquinolinones and tetrahydrobenzazepinones represented by the formula

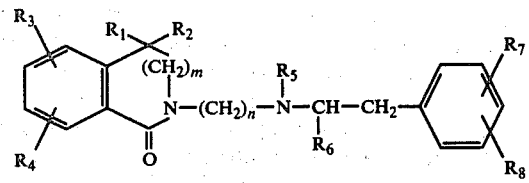

wherein $R_1$, $R_2$ and $R_6$, which may be identical to or different from each other, are each hydrogen or lower alkyl;

$R_3$ is lower alkoxy;

$R_4$ is lower alkoxy or, together with $R_3$, methylenedioxy or ethylenedioxy;

$R_5$ is hydrogen, lower alkyl or benzyl;

$R_7$ is hydrogen or lower alkoxy;

$R_8$ is hydrogen, lower alkoxy or, together with $R_7$, methylenedioxy or ethylenedioxy;

m is 1 or 2; and n is 2 or 3;

and non-toxic, pharmacologically acceptable acid addition salts thereof.

By "lower alkyl" we mean primarily alkyl of 1 to 3 carbon atoms; similarly, "lower alkoxy" is intended to designate primarily alkoxy of 1 to 3 carbon atoms.

A preferred sub-genus is constituted by compounds of the formula I,
where $R_1$, $R_2$ and $R_6$ are each hydrogen, methyl, ethyl, n-propyl or isopropyl;

$R_3$ is methoxy, ethoxy, n-propoxy or isopropoxy;

$R_4$ is methoxy, ethoxy, n-propoxy, isopropoxy or, together with $R_3$, methylenedioxy or ethylenedioxy;

$R_5$ is hydrogen, methyl, ethyl, n-propyl, isopropyl or benzyl;

$R_7$ is hydrogen, methoxy, ethoxy, n-propoxy or isopropoxy;

$R_8$ is methoxy, ethoxy, n-propoxy, isopropoxy or, together with $R_7$, methylenedioxy or ethylenedioxy;

m is 1 or 2; and n is 2 or 3;

and non-toxic, pharmacologically acceptable acid addition salts thereof.

A further, especially preferred sub-genus is constituted by compounds of the formula I,
where $R_1$, $R_2$ and $R_5$ are each hydrogen or methyl;

$R_3$ is methoxy;

$R_4$ is methoxy or, together with $R_3$, methylenedioxy or ethylenedioxy;

$R_6$ is hydrogen; $R_7$ is hydrogen or methoxy;

$R_8$ is methoxy or, together with $R_7$, methylenedioxy or ethylenedioxy;

m is 1 or 2; and n os 2 pr 3;

and non toxic, pharmacologically acceptable acid addition salts thereof.

The compounds embraced by formula I may be prepared by the following methods:

Method A

By reacting a compound of the formula

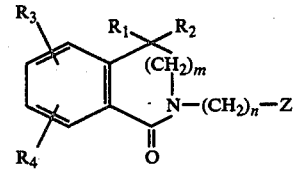

wherein $R_1$, $R_2$, $R_3$, $R_4$, m and n have the same meanings as in formula I, and Z is a leaving group, such as chlorine, bromine, iodine, alkylsulfonyloxy or arylsulfonyloxy, with a phenylalkylamine of the formula

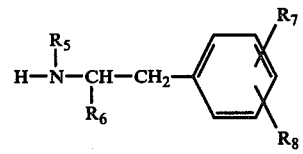

wherein $R_5$, $R_6$, $R_7$ and $R_8$ have the same meanings as in formula I.

The reaction is advantageously carried out in the presence of solvent, such as ether, tetrahydrofuran, methyl formamide, dimethyl formamide, dimethyl sulfoxide, chlorobenzene or benzene, and at temperatures between $-50°$ and $+250°$ C. depending on the reactivity of substituent Z, but preferably at the boiling point of the particular solvent which is used. The presence of an acid-binding agent, such as an alkali metal alcoholate, an alkali metal hydroxide, an alkali metal carbonate, especially potassium carbonate, or a tertiary organic base such as triethlamine or pyridine, or of a reaction accelerator such as potassium iodide is of advantage.

Method B

By reacting a compound of the formula

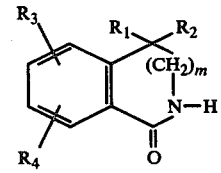

wherein $R_1$, $R_2$, $R_3$, $R_4$ and m have the same meanings as in formula I, with

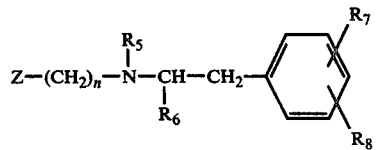

wherein $R_5$, $R_6$, $R_7$ and $R_8$ have the same meanings as in formula I, and Z has the same meanings as in formula II.

The reaction is advantageously carried out in the presence of a solvent, such as acetone, dimethyl, formamide, dimethyl sulfoxide or chlorobenzene, and at temperatures between 0° and 150° C., depending on the reactivity of the group Z, but preferably at the boiling point of the particular solvent which is used. The presence of an acid-binding agent such as an alkali metal alcoholate, an alkali metal hydroxide, an alkali metal carbonate, especially potassium carbonate, an alkali metal amide, an alkali metal hydride, especially sodium hydride, or a tertiary organic base such as triethylamine or pyridine, or of a reaction accelerator such as potassium iodide is of advantage.

Method C

By reacting an aldehyde of the formula

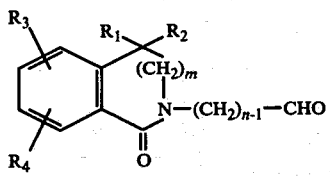

wherein $R_1$, $R_2$, $R_3$, $R_4$ and m have the same meanings as in formula I, or an acetal thereof, with a phenylalkylamine of the formula

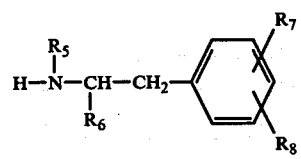

wherein $R_5$, $R_6$, $R_7$ and $R_8$ have the same meanings as in formula I, in the presence of catalytically activated hydrogen.

The reductive amination is carried out with hydrogen in the presence of a hydrogenation catalyst, for example, with hydrogen in the presence of palladium-on-charcoal, at a hydrogen pressure of 5 atmospheres, in the presence of a solvent such as methanol, ethanol or dioxane, and at temperatures between 0° and 100° C., but preferably at temperatures between 20° and 80° C.

Method D

By reacting an amine of the formula

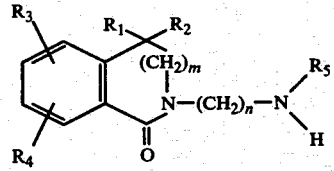

wherein $R_1$, $R_2$, $R_3$, $R_4$, $R_5$, m and n have the same meanings as in formula I, with an aralkyl compound of the formula

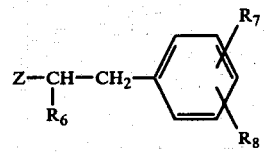

wherein $R_6$, $R_7$ and $R_8$ have the same meanings as in formula I, and

Z has the same meanings as in formula II.

The reaction is advantageously carried out in the presence of a solvent, such as acetone, methylene chloride, dimethyl formamide, dimethyl sulfoxide or chlorobenzene, and at temperatures between 0° and 150° C., depending on the reactivity of the group Z, but preferably at the boiling point of the particular solvent which is used. The presence of an acid-binding agent, such as an alkali metal alcoholate, an alkali metal hydroxide, an alkali metal carbonate, especially potassium carbonate, or a tertiary organic base such as triethylamine or pyridine, or of a reaction accelerator such as potassium iodide is of advantage.

Method E

By reducing a compound of the formula

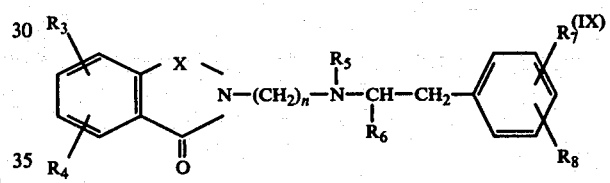

wherein $R_3$, $R_4$, $R_5$, $R_6$, $R_7$, $R_8$ and n have the same meanings as in formula I, and X is

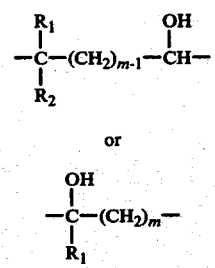

where $R_1$, $R_2$ and m have the same meanings as in formula I.

The reduction is preferably carried out in a solvent such as glacial acetic acid, water, ethanol or ethyl acetate, with nascent hydrogen, for example generated in situ with zinc/glacial acetic acid, tin/hydrochloric acid or tin(II) chloride/hydrochloric acid, or with catalytically activated hydrogen, for instance with hydrogen in the presence of palladium-on-charcoal, and a hydrogen pressure of 1 to 7 atmospheres, at temperatures between 0° and 150° C., but preferably at temperatures between 25 and 110° C.

Method F

By reacting an aralkyl compound of the formula

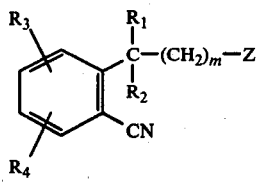

wherein $R_1$, $R_2$, $R_3$, $R_4$ and m have the same meanings as in formula I, and Z has the same meanings as in formula II, with an alkylenediamine of the formula

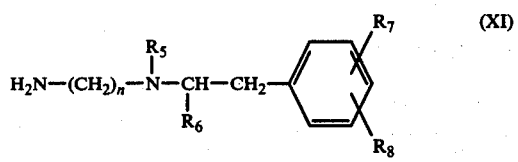

wherein $R_5$, $R_6$, $R_7$, $R_8$ and n have the same meanings as in formula I, followed by hydrolysis of the intermediate 1-imino compound.

The reaction is advantageously carried out in the presence of a solvent, such as acetone, ethanol, dimethyl formamide, dimethyl sulfoxide or methylene chloride, and at elevated temperatures, for instance at temperatures between 50° and 150° C. The presence of an acid-binding agent, such as alkali metal alcoholate, an alkali metal hydroxide, an alkali metal carbonate or a tertiary organic base, such as triethylamine or pyridine, or of a reaction accelerator such as potassium iodide is of advantage.

The subsequent hydrolysis is carried out in the presence of a base, such as potassium carbonate, or in the presence of an acid, such as hydrochloric acid, in an aqueous medium such as ethanol/water or dioxane/water, and at temperatures between 50° C. and the boiling point of the particular solvent which is used.

Method G

By reacting an aralkyl compound of the formula

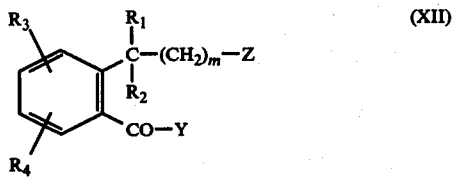

wherein $R_1$, $R_2$, $R_3$, $R_4$ and m have the same meanings as in formula I, Z has the same meanings as in formula II, and Y is a leaving-group, such as chlorine, bromine, iodine, alkoxy or aryloxy, with an alkylenediamine of the formula XI.

The reaction is advantageously carried out in the presence of a solvent, such as acetone, dimethyl formamide, dimethyl sulfoxide or methylene chloride, at elevated temperatures, for instance at temperatures between 50 and 150° C. The presence of an acid-binding agent, such as an alkali metal alcoholate, an alkali metal hydroxide such as potassium hydroxide, an alkali metal carbonate, or a tertiary organic base such as triethylamine or pyridine, or of a reaction accelerator such as potassium iodide, is of advantage.

The benzamide intermediate formed in situ, of the formula

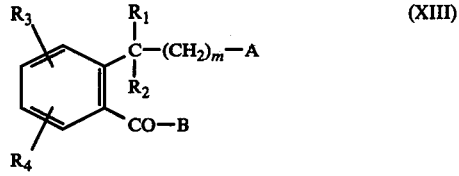

wherein $R_1$, $R_2$, $R_3$, $R_4$ and m have the same meanings as in formula I, one of A and B has the meanings defined above for Z and Y in formula XII, and the other of A and B is

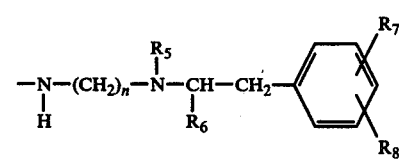

where $R_5$, $R_6$, $R_7$, $R_8$ and n have the same meanings as in formula I, may, if desired, be isolated before being further reacted.

Method H

By reacting a carbonyl compound of the formula

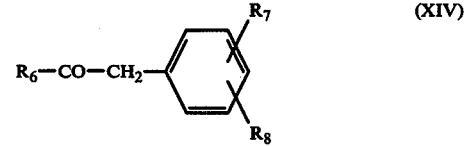

wherein $R_6$, $R_7$ and $R_8$ have the same meanings as in formula I, with a compound of the formula VII in the presence of catalytically activated hydrogen.

The reductive amination is carried out with hydrogen in the presence of a hydrogenation catalyst, for instance with hydrogen in the presence of palladium-on-charcoal at a hydrogen pressure of 5 atmospheres, in the presence of a solvent such as methanol, ethanol or dioxane, and at temperatures between 0 and 100° C., but preferably at temperatures between 20 and 80° C.

If the end product of methods A through H is a compound of the formula I wherein $R_5$ is benzyl, the same may be de-benzylated to yield the corresponding compound wherein $R_5$ is hydrogen. The de-benzylation is preferably effected by means of catalytic hydrogenation, for example with hydrogen in the presence of a catalyst such as palladized charcoal, in a solvent such as ethanol or ethyl acetate, at a temperature between 25 and 75° C., and at a hydrogen pressure of 1 to 7 atmospheres.

On the other hand, if the end product of methods A through H is a compound of the formula I wherein $R_5$ is hydrogen, the same may be alkylated at the bridge nitrogen atom to form the corresponding compound where $R_5$ is alkyl. The alkylation is carried out with a conventional alkylating agent, for example with an alkyl halide such as methyl iodide, ethyl iodide or isopropyl bromide, or with a dialkylsufate such as dimethylsulfate, in a solvent such as acetone, dimethylformamide or dioxane, optionally in the presence of an inorganic or tertiary organic base, at a temperature between 0 and 50° C. A methylation may also be effected by reaction with a mixture of formaldehyde and formic acid, preferably at the boiling point of said mixture.

The compounds embraced by formula I are organic bases and therefore form acid addition salts with inorganic or organic acids. Examples of non-toxic, pharmacologically acceptable acid addition salts are those formed with hydrochloric acid, phosphoric acid, hydrobromic acid, sulfuric acid, lactic acid, tartaric acid, maleic acid, 8-chlorotheophylline or the like.

The starting compounds of the formulas II through XIV are either described in the literature or may be prepared by known methods, as described in the examples below.

For example, a starting compound of the formula IV may be obtained by cyclization of a compound of the formula

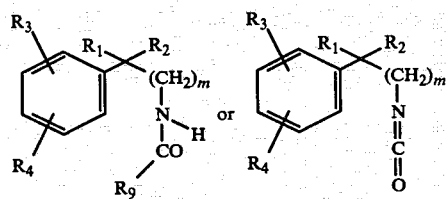

wherein

R$_1$, R$_2$, R$_3$, R$_4$ and m have the same meanings as in formula I, and

R$_9$ is alkoxy or alkylthio, in the presence of an acid condensation agent such as polyphosphoric acid [see S. Karady et al., J. org. Chem. 27, 3720 (1962)]. A compound of the formula IV thus obtained may be converted into a compound of the formula II, VI or VII by means of alkylation.

A starting compound of the formula IX may be obtained by selective reduction of a corresponding carbonyl derivative (see Belgian Pat. No. 819,651) with a complex metal hydride.

The following examples illustrate the present invention and will enable others skilled in the art to understand it more completely. It should be understood, however, that the invention is not limited solely to the particular examples given below.

EXAMPLE 1

1-[6,7-Dimethoxy-3,4-dihydro-2H-isoquinolin-1-one-2-yl]-3-[N-methyl-N-(2-(3,4-dimethoxy-phenyl)-ethyl)-amino]-propane and its hydrochloride by method A (a) 2.1 gm (44 millimols) of sodium hydride were added to a solution of 8.0 gm (41 millimols) of 6,7-dimethoxy-3,4-dihydro-2H-isoquinolin-1-one in 100 ml of dimethyl formamide, and the mixture was heated at 80° C. for 30 minutes. Then, 20 ml of 1-bromo-3-chloro-propane were added dropwise, and the mixture was heated at 100° C. for 3 hours. The solvent was then removed in vacuo, the solid residue was digested in water, and the aqueous mixture was extracted with chloroform several times. The combined organic extracts were dried over sodium sulfate and evaporated to dryness, and the evaporation residue was purified by chromatography on silica gel (chloroform/methanol = 150/1), yielding 3.2 gm of 1-(6,7-dimethoxy-3,4-dihydro-2H-isoquinolin-1-one-2-yl)-3-chloro-propane as a viscous oil having an R$_f$-value of 0.8 (ethyl acetate).

(b) A mixture consisting of a solution of 1.4 gm (4.95 millimols) of 1-(6,7-dimethoxy-3,4-dihydro-2H-isoquinolin-1-one-2-yl)-3-chloro-propane in 50 ml of chlorobenzene 0.97 gm (5.0 millimols) of N-(3,4-dimethoxy-phenylethyl)-N-methyl-amine, 3.0 gm of potassium carbonate and a spatula tipful of potassium iodide was refluxed for 30 hours. After cooling, the solid phase was filtered off, and the filtrate was evaporated. The residue was purified by chromatography on silica gel (chloroform/methanol = 50/1 to 30/1), the combined main fractions were evaporated and the base was precipitated with ethereal hydrochloric acid as its hydrochloride of the formula

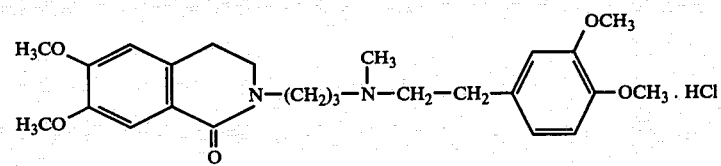

having a melting point of 178–179° C. Yield: 0.4 gm (21% of theory).

Example 2

1-[6,7-Dimethoxy-3,4-dihydro-2H-isoquinolin-1-one-2-yl]-3-[N-(2-(3,4-dimethoxy-phenyl)-ethyl)-amino]-propane and its hydrochloride (a) 1-[6,7-Dimethoxy-3,4-dihydro-2H-isoquinolin-1-one-2-yl]-3-[N-benzyl-N-(2-(3,4-dimethoxy-phenyl)-ethyl)-amino]-propane was prepared analogous to Example 1 (b) by reacting 1-(6,7-dimethoxy-3,4-dihydro-2H-isoquinolin-1-one-2-yl)-3-chloropropane with N-(3,4-dimethoxy-phenylethyl)-N-benzyl-amine in chlorobenzene in the presence of potassium carbonate. Yield: 2.2 gm (69.8% of theory); R$_f$-value (chloroform/methanol = 19:1): 0.8.

(b) 1 gm of palladium-on-charcoal (30%) was added to a solution of 2.17 gm (4.2 millimols) of 1-[6,7-dimethoxy-3,4-dihydro-2H-isoquinolin-1-one-2-yl]-3-[N-benzyl-N-(2-(3,4-dimethoxy-phenyl)-ethyl)-amino]-propane in 50 ml of methanol, and hydrogen was introduced into the mixture for 4 hours at room temperature. After the absorption of hydrogen had ceased, the catalyst was filtered off, and the filtrate was evaporated in vacuo. The residue was dissolved in acetone, and the hydrochloride was precipitated therefrom by addition of ethereal hydrochloric acid, yielding 0.62 gm (32% of theory) of 1-[6,7-Dimethoxy-3,4-dihydro-2H-isoquinolin-1-one-2-yl]-3-[N-(2-(3,4-dimethoxy-phenyl)-ethyl)-amino]-propane hydrochloride, m.p. 132–134° C.

EXAMPLE 3

1-[4,4-Dimethyl-6,7-dimethoxy-3,4-dihydro-2H-isoquinolin-1-one-2-yl]-3-[N-methyl-N-(2-(3,4-dimethoxy-phenyl)-ethyl)-amino]-propane and its hydrochloride by method E (a) 0.49 gm (13.0 millimols) of sodium borohydride were added at 0° C. to a solution of 4.0 gm (8.2 millimols) of 1-[4,4-dimethyl-6,7-dimethoxy-1,3-dioxo-(2H,4H)-isoquinolin-2-yl]-3-[N-methyl-N-(2-(3,4-dimethoxy-phenyl)-ethyl)-amino]-propane in a mixture of 100 ml of dioxane and 20 ml of water. The mixture was stirred at room temperature for 8 hours and subsequently admixed with 100 ml of 2 N hydrochloric acid. After extraction with chloroform, the organic extract was dried over sodium sulfate and evaporated in vacuo, leaving as a residue 3.25 gm (80% of theory) of 1-[3-hydroxy-4,4-dimethyl-6,7-dimethoxy-3,4-dihydro-2H-isoquinolin-1-one-2-yl]-3-[N-methyl-N-(2-(3,4-dimethoxy-phenyl)-ethyl)-amino]-propane.

(b) 2.3 gm of zinc dust were added to a solution of 3.25 gm (6.7 millimols) of 1-[3-hydroxy-4,4-dimethyl-6,7-dimethoxy-3,4-dihydro-2H-isoquinolin-1-one-2-yl]-3-[N-methyl-N-(2-(3,4-dimethoxy-phenyl)-ethyl)-amino]-propane in 80 ml of glacial acetic acid, and the mixture was refluxed for 4 hours. For separation of the zinc dust the hot solution was filtered, and the filtrate was evaporated to dryness in vacuo. The residue was subsequently dissolved in chloroform, and the chloroform solution was extracted with a saturated aqueous sodium bicarbonate solution and with water, dried with sodium sulfate and evaporated. The residue was purified by chromatography on silica gel (chloroform/methanol = 19:1), and the hydrochloride was precipitated from the eluate with ethereal hydrochloric acid, yielding 2.2 gm (70% of theory) of the compound of the formula

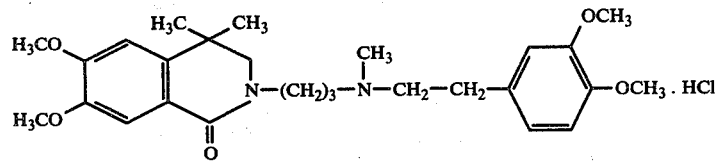

which had a melting point of 70° C. (decomp.) and an $R_f$-value of 0.45 (chloroform/methanol = 9/1).

Using procedures analogous to those described in Examples 1, 2 and 3, the following compounds of the formula I were also prepared:

(4) 1-[6,7-Ethylenedioxy-3,4-dihydro-2H-isoquinolin-1-one-2-yl]-3-[N-methyl-N-(2-(3,4-dimethoxy-phenyl)-ethyl)-amino]-propane hydrochloride, $R_f$-value: 0.40 (chloroform/methanol = 19:1).

(5) 1-[6,7-Methylenedioxy-3,4-dihydro-2H-isoquinolin-1-one-2-yl]-3-[N-methyl-N-(2-(3,4-dimethoxy-phenyl)-ethyl)-amino]-propane hydrochloride, $R_f$ value: 0.25 (chloroform/methanol = 19:1).

(6) 1-[6,7-Dimethoxy-3,4-dihydro-2H-isoquinolin-1-one-2-yl]-2-[N-methyl-N-(2-(3,4-dimethoxy-phenyl)-ethyl-amino]-ethane hydrochloride, $R_f$-value: 0.25 (chloroform/methanol = 19:1).

(7) 1-[6,7-Dimethoxy-3,4-dihydro-2H-isoquinolin-1-one-2-yl]-2-[N-(2-(3,4-dimethoxy-phenyl)-ethyl)-amino]-ethane hydrochloride, $R_f$-value: 0.15 (chloroform/methanol = 19:1).

(8) 1-[6,7-Dimethoxy-3,4-dihydro-2H-isoquinolin-1-one-2-yl]-3-[N-methyl-N-(2-(4-methoxy-phenyl)-ethyl-amino]-propane hydrochloride, $R_f$-value: 0.35 (chloroform/methanol = 19:1).

(9) 1-[6,7-Dimethoxy-3,4-dihydro-2H-isoquinolin-1-one-2-yl]-3-[N-methyl-N-(2-(3-methoxy-phenyl)-ethyl)-amino]-propane hydrochloride, $R_f$-value: 0.30 (chloroform/methanol = 19:1).

(10) 1-[6,7-Dimethoxy-3,4-dihydro-2H-isoquinolin-1-one-2-yl]-3-[N-methyl-N-(2-(3,4-methylenedioxy-phenyl)-ethyl-amino]-propane hydrochloride, $R_f$-value: 0.40 (chloroform/methanol = 19:1).

(11) 1-[4,4-Dimethyl-6,7-dimethoxy-3,4-dihydro-2H-isoquinolin-1-one-2-yl]-3-[N-methyl-N-(2-(3,4-dimethoxy-phenyl)-ethyl)-amino]-propane hydrochloride, $R_f$-value: 0.25 (chloroform/methanol = 19:1).

(12) 1-[4,4-Dimethyl-6,7-dimethoxy-3,4-dihydro-2H-isoquinolin-1-one-2-yl]-3-[N-(2-(3,4-dimethoxy-phenyl)-ethyl)-amino]-propane hydrochloride, $R_f$-value: 0.20 (chloroform/methanol = 19:1).

Calcuated: C-62.20%;H-7.63%; N-5.58%. Found: C-62.80%;H-7.95%; N-5.31%.

(13) 1-[4,4-Dimethyl-6,7-dimethoxy-3,4-dihydro-2H-isoquinolin-1-one-2-yl]-2-[N-methyl-N-(2-(3,4-dimethoxy-phenyl)-ethyl)-amino]-ethane hydrochloride, $R_f$-value: 0.40 (chloroform/methanol = 9:1).

(14) 1-[4,4-Dimethyl-6,7-dimethoxy-3,4-dihydro-2H-isoquinolin-1-one-2-yl]-2-[N-(2-(3,4-dimethoxy-phenyl-ethyl)-amino]-ethane hydrochloride, $R_f$-value: 0.20 (chloroform/methanol = 9:1).

(15) 1-[7,8-Dimethoxy-1,2,3,4-tetrahydro-5H-2-benzazepin-1-one-2-yl]-3-[N-methyl-N-(2-(3,4-dimethoxy-phenyl)-ethyl)-amino]-propane hydrochloride, $R_f$ value: 0.20 (chloroform/methanol = 9:1), IR-spectrum (potassium bromide): >CO at 1640 cm$^{-1}$.

(16) 1-[7,8-Dimethoxy-1,2,3,4-tetrahydro-5H-2-benzazepin-1-one-2-yl]-3-[N-(3,4-dimethoxy-phenyl)-ethyl)-amino]-propane hydrochloride, $R_f$-value: 0.10 (chloroform/methanol = 3:1), of the formula

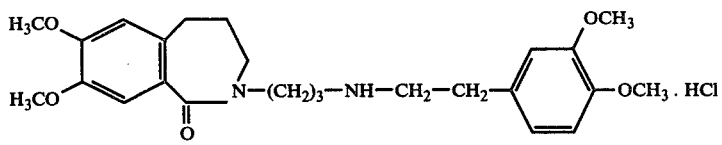

The compounds embraced by formula I and their nontoxic, pharmacologically acceptable acid addition salts have useful pharmacodynamic properties. More particularly, they exhibit selective bradycardiac and mild antihypertensive activities in warm-blooded animals, such as cats.

The bradycardiac properties of the compounds of this invention were ascertained by the test method described below, and the table shows the results of the tests for a few representative species of the genus, where

- A = 1-[6,7-Dimethoxy-3,4-dihydro-2H-isoquinolin-1-one-2-yl]-3-[N-methyl-N-(2-(3,4-dimethoxy-phenyl)-ethyl)-amino] propane hydrochloride;
- B = 1-[6,7-Dimethoxy-3,4-dihydro-2H-isoquinolin-1-one-2-yl]-3-[N-(2-(3,4-dimethoxy-phenyl)-ethyl)-amino] propane hydrochloride;
- C = 1-[4,4-Dimethyl-6,7-dimethoxy-3,4-dihydro-2H-isoquinolin-1-one-2-yl]-3-[N-methyl-N-(2-(3,4-dimethoxy-phenyl)-ethyl)-amino]-propane hydrochloride;
- D = 1-[4,4-Dimethyl-6,7-dimethoxy-3,4-dihydro-2H-isoquinolin-1-one-2-yl]-3-[N-(2-(3,4-dimethoxy-phenyl)-ethyl)-amino]-propane hydrochloride; and
- E = 1-[7,8-Dimethoxy-1,2,3,4-tetrahydro-5H-2-benzazepin-1-one-2-yl]-3-[N-methyl-N-(2-(3,4-dimethoxy-phenyl)-ethyl)-amino]-propane hydrochloride.

The effect of the test compound on the heart rate was tested at various dosage levels on 2–4 cats of both sexes per dose. The average body weight of the cats was 2.5–3.5 kg. For this purpose the animals were anesthetized with nembutal (30 mgm/kg i.p.) and chloralose-urethane (40 mgm/ml chloralose + 200 mgm/ml urethane as required). The test compound in aqueous solution was injected into the Vena saphena (i.v.) or duodenum (i.p.).

The heart rate was registered before and after administration of the test compound on a Grass-polygraph by means of a Grass-tachograph from the electrocardiogram (precordial lead). The following table shows the results obtained

| Compound | Dosage mgm/kg | Decrease in heart rate beats/minute | Duration of effective action in minutes |
|---|---|---|---|
| A | 0.1 i.v. | − 14 | 30 |
| A | 0.3 i.v. | − 31 | 30 |
| A | 1.0 i.v. | − 53 | 50 |
| A | 10.0 i.v. | − 116 | 70 |
| A | 3.0 i.d. | − 44 | 60 |
| A | 30.0 i.d. | − 28 | 60 |
| B | 0.3 i.v. | − 11 | 22 |
| B | 1.0 i.v. | − 14 | 17 |
| B | 2.0 i.v. | − 24 | 43 |
| C | 0.3 i.v. | − 7 | 8 |
| C | 1.0 i.v. | − 18 | 11 |
| C | 3.0 i.v. | − 32 | 18 |
| D | 1.0 i.v. | − 2 | 6 |
| D | 3.0 i.v. | − 28 | 16 |
| E | 1.0 i.v. | − 15 | 30 |
| E | 2.0 i.v. | − 28 | 20 |

Additionally, it should be noted that at all dosage levels the test compounds were tolerated very well and produced no toxic side-effects. The $LD_{50}$ for compound A in mice, for example, was determined to be 53 mgm/kg i.v. with an observation time of 14 days.

Thus, the compounds of this invention are useful for the treatment of pectanginal disorders, especially for the treatment of chronic coronary insufficiency.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 4.17 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE I

Tablets

The tablet composition is compounded from the following ingredients:

| | |
|---|---|
| 1-[6,7-Dimethoxy-3,4-dihydro-2H-isoquinolin-1-one-2-yl]-3-[N-methyl-N-(2-(3,4-dimethoxy-phenyl)-ethyl)-amino]-propane hydrochloride | 100.0 parts |
| Lactose | 50.0 parts |
| Polyvinylpyrrolidone | 5.0 parts |
| Carboxymethyl cellulose | 19.0 parts |
| Magnesium stearate | 1.0 parts |
| Total | 175.0 parts |

Preparation

The active ingredient and the lactose are intimately admixed with each other, the mixture is uniformly moistened with an aqueous solution of the polyvinylpyrrolidone, and the moist mass is granulated by passing it through a fine-mesh screen. The granulate is then dried and admixed with the remaining ingredients, and the composition is compressed into 175 mgm-tablets in a conventional tablet making machine. Each tablet is an oral dosage unit composition containing 100 mgm of the active ingredient.

EXAMPLE II

Coated pills

The pill core composition is compounded from the following ingredients:

| | |
|---|---|
| 1-[6,7-Dimethoxy-3,4-dihydro-2H-isoquinolin-1-one-2-yl]-3-[N-methyl-N-(2-(3,4-dimethoxy-phenyl)-ethyl)-amino]-propane hydrochloride | 50.0 parts |
| Corn starch, dry | 20.0 parts |
| Soluble starch | 2.0 parts |
| Carboxymethyl cellulose | 7.0 parts |
| Magnesium stearate | 1.0 parts |
| Total | 80.0 parts |

Preparation

The ingredients are compounded in analogy to the preceding example, and the composition is compressed into 80 mgm-pill cores which are subsequently coated with a thin shell consisting essentially of a mixture of sugar and gumarabic. Each coated pill is an oral dosage unit composition containing 50 mgm of the active ingredient.

EXAMPLE III

Suppositories

The suppository composition is compounded from the following ingredients:

| |
|---|
| 1-[6,7-Dimethoxy-3,4-dihydro-2H-isoquinolin-1-one-2-yl]-3-[N-methyl-N-(2-(3,4-dimethoxy-phenyl)- |

-continued

| | |
|---|---|
| ethyl)-amino]-propane hydrochloride | 150.0 parts |
| Suppository base (e.g. cocoa butter) | 1550.0 parts |
| Total | 1700.0 parts |

Preparation

The active ingredient is uniformly blended into the molten suppository base, and 1.7 gm-portions of the liquid mixture are poured into cooled suppository molds and allowed to harden therein. Each suppository is a rectal dosage unit composition containing 150 mgm of the active ingredient.

EXAMPLE IV

Suspension

The suspension is compounded from the following ingredients:

| | |
|---|---|
| 1-[6,7-Dimethoxy-3,4-dihydro-2H-isoquinolin-1-one-2-yl]-3-[N-methyl-N-(2-(3,4-dimethoxy-phenyl)-ethyl)-amino]-propane hydrochloride | 5.0 parts |
| Carboxymethyl cellulose | 0.1 parts |
| Methyl p-hydroxybenzoate | 0.05 parts |
| Propyl p-hydroxybenzoate | 0.01 parts |
| Sugar | 10.0 parts |
| Glycerin | 5.0 parts |
| Sorbitol solution 70% | 20.0 parts |
| Flavoring | 0.03 parts |
| Distilled water q.s.ad | 100.0 parts by vol. |

Preparation

While stirring, the p-hydroxybenzoates, the glycerin and the carboxymethyl cellulose are dissolved in the distilled water at 70° C. The resulting solution is cooled to room temperature and, while stirring, the active ingredient is added and homogeneously dispersed therein. Thereafter, the sugar, the sorbitol solution and the flavoring are added and dissolved in the dispersion, and the composition is deaerated by stirring in vacuo. The suspension is an oral dosage unit composition, 5 ml of which contain 250 mgm of the active ingredient.

Any one of the other compounds embraced by formula I or a non-toxic, pharmacologically acceptable acid addition salt thereof may be substituted for the particular active ingredient in Examples I through IV. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without department from the spirit of the invention or the scope of the appended claims.

We claim:

1. A compound of the formula

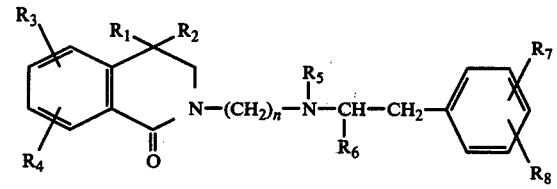

wherein
$R_1$, $R_2$ and $R_6$ are each hydrogen or alkyl of 1 to 3 carbon atoms;
$R_3$ is alkoxy of 1 to 3 carbon atoms;
$R_4$ is alkoxy of 1 to 3 carbon atoms, or together with $R_3$, methylenedioxy or ethylenedioxy;
$R_5$ is hydrogen, alkyl or 1 to 3 carbon atoms or benzyl;
$R_7$ is hydrogen or alkoxy of 1 to 3 carbon atoms;
$R_8$ is alkoxy of 1 to 3 carbon atoms, or together with $R_7$, methylenedioxy or ethylenedioxy; and
n is 2 or 3;
or a non-toxic, pharmacologically acceptable acid addition salt thereof.

2. A compound of claim 1, wherein $R_1$ and $R_2$ are each hydrogen or methyl;
$R_3$ is methoxy;
$R_4$ is methoxy or, together with $R_3$, methylenedioxy or ethylenedioxy;
$R_5$ is hydrogen, methyl or benzyl;
$R_6$ is hydrogen;
$R_7$ is hydrogen or methoxy;
$R_8$ is methoxy or, together with $R_7$, methylenedioxy or ethylenedioxy;
n is 2 or 3.

3. A compound of claim 1, which is 1-[6,7-dimethoxy-3,4-dihydro-2H-isoquinolin-1-one-2-yl]-3-[N-methyl-N-(2-(3,4-dimethoxy-phenyl)-ethyl)-amino]-propane or a non-toxic, pharmacologically acceptable acid addition salt thereof.

4. A compound of claim 1, which is 1-[6,7-dimethoxy-3,4-dihydro-2H-isoquinolin-1-one-2-yl]-3-[N-(2-(3,4-dimethoxy-phenyl)-ethyl)-amino]-propane or a non-toxic, pharmacologically acceptable acid addition salt thereof.

5. A pharmaceutical dosage unit composition consisting essentially of an inert pharmaceutical carrier and an effective bradycardiac amount of a compound of claim 1.

6. The method of reducing the heart rate of a warm-blooded animal in need thereof, which comprises perorally parenterally or rectally administering to said animal an effective bradycardiac amount of a compound of claim 1.

* * * * *